(12) United States Patent
Samson et al.

(10) Patent No.: US 6,267,747 B1
(45) Date of Patent: Jul. 31, 2001

(54) AORTIC CATHETER WITH POROUS AORTIC ROOT BALLOON AND METHODS FOR INDUCING CARDIOPLEGIC ARREST

(75) Inventors: Wilfred J. Samson, Saratoga; Janine Robinson, Half Moon Bay; Steve Baker; James J. Leary, both of Sunnyvale, all of CA (US)

(73) Assignee: Cardeon Corporation, Cupertino, CA (US)

( * ) Notice: Subject to any disclaimer, the term of this patent is extended or adjusted under 35 U.S.C. 154(b) by 0 days.

(21) Appl. No.: 09/306,696

(22) Filed: May 6, 1999

Related U.S. Application Data

(60) Provisional application No. 60/084,939, filed on May 11, 1998.

(51) Int. Cl.[7] .................................................. A61M 29/00
(52) U.S. Cl. .............................. 604/103.07; 604/103.01; 606/192
(58) Field of Search ................. 604/96.01, 99.04, 604/264, 523, 529, 101.01–101.02, 103.01, 103.06, 103.07, 103.08, 103.1, 103.11, 4.01, 5.01, 6.16, 101.05, 915, 916; 606/194, 192

(56) References Cited

U.S. PATENT DOCUMENTS

| | | |
|---|---|---|
| Re. 35,352 * | 10/1996 | Peters . |
| 3,810,474 * | 5/1974 | Cross . |
| 4,364,392 | 12/1982 | Strother et al. .................. 128/325 |
| 4,693,243 * | 9/1987 | Buras . |
| 4,694,827 * | 9/1987 | Weiner et al. . |
| 4,787,388 | 11/1988 | Hofmann ........................... 128/344 |
| 4,821,722 | 4/1989 | Miller et al. ...................... 128/344 |
| 4,994,033 | 2/1991 | Shockey et al. ................... 604/101 |
| 5,049,132 * | 9/1991 | Shaffer et al. .................... 604/101 |
| 5,087,244 * | 2/1992 | Wolinsky et al. . |
| 5,092,841 * | 3/1992 | Spears . |
| 5,213,576 | 5/1993 | Abuiso et al. ...................... 604/96 |
| 5,232,444 * | 8/1993 | Just et al. . |
| 5,306,241 * | 4/1994 | Samples . |
| 5,308,356 * | 5/1994 | Blackshear, Jr. et al. . |
| 5,318,531 | 6/1994 | Leone ................................. 604/96 |
| 5,352,199 * | 10/1994 | Tower . |
| 5,354,774 | 10/1994 | Deckelbaum et al. ............. 514/455 |
| 5,405,472 | 4/1995 | Leone ................................ 156/218 |
| 5,458,568 | 10/1995 | Racchini et al. .................... 604/19 |
| 5,514,707 | 5/1996 | Deckelbaum et al. ............. 514/455 |
| 5,547,472 | 8/1996 | Onishi et al. ....................... 604/93 |
| 5,558,642 | 9/1996 | Schweich et al. .................. 604/96 |
| 5,569,198 | 10/1996 | Racchini ............................. 604/96 |
| 5,584,803 * | 12/1996 | Stevens et al. ....................... 604/4 |
| 5,611,775 | 3/1997 | Machold et al. ................... 604/53 |

(List continued on next page.)

FOREIGN PATENT DOCUMENTS 86201487   8/1986   (EP) .......................... A61M/25/00

OTHER PUBLICATIONS

Technical Specifications Percluder® aortic occluding balloon, Datascope Corp. © 1987 Datascope Corp.

Primary Examiner—Anhtuan T. Nguyen
Assistant Examiner—LoAn H. Thanh
(74) Attorney, Agent, or Firm—Fulwider Patton Lee & Utecht, LLP

(57) ABSTRACT

The present invention relates to a catheter or cannula system that facilitates cardiopulmonary bypass surgeries and enables prolonged circulatory support of the heart. More specifically, the present invention provides an aortic catheter system including a porous aortic root balloon capable of occluding the aorta, delivering cardioplegia and providing tactile feedback and helping to maintain the competency of regurgitant aortic valves.

24 Claims, 12 Drawing Sheets

U.S. PATENT DOCUMENTS

| | | | |
|---|---|---|---|
| 5,653,689 | 8/1997 | Buelna et al. | 604/96 |
| 5,669,874 | 9/1997 | Feiring | 604/21 |
| 5,674,198 | 10/1997 | Leone | 604/101 |
| 5,704,908 | 1/1998 | Hofmann et al. | 604/19 |
| 5,709,653 | 1/1998 | Leone | 604/20 |
| 5,728,068 | 3/1998 | Leone et al. | 604/101 |
| 5,792,106 * | 8/1998 | Mische | |
| 5,797,868 | 8/1998 | Leone | 604/21 |
| 5,866,561 | 2/1999 | Ungs | 514/182 |
| 5,868,704 | 2/1999 | Campbell et al. | 604/96 |
| 5,876,374 | 3/1999 | Alba et al. | 604/96 |

\* cited by examiner

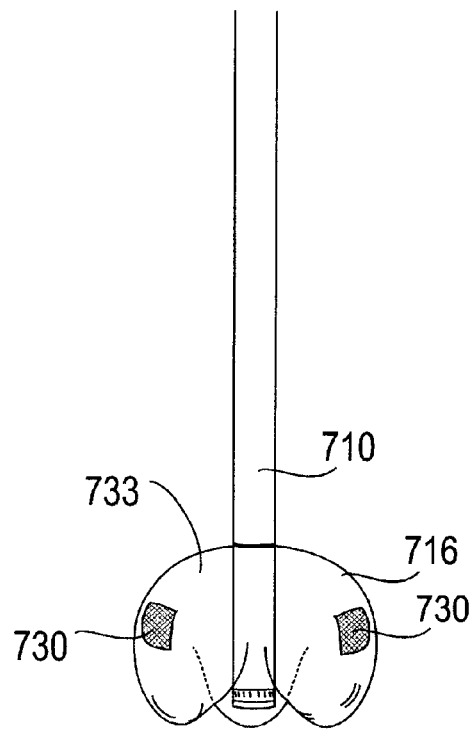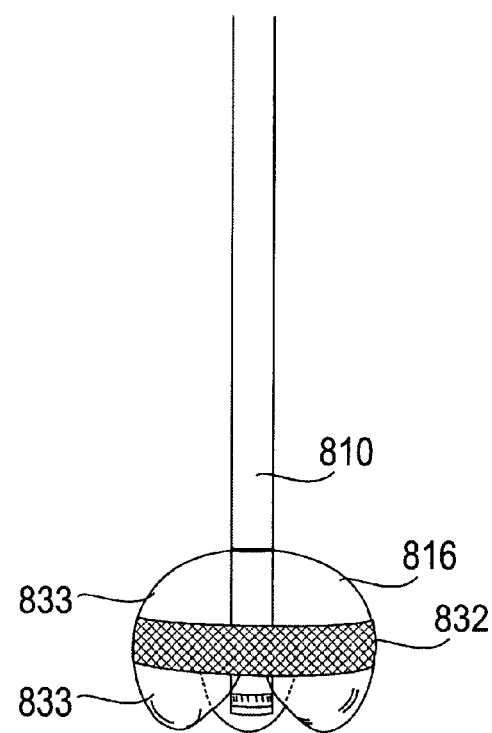
FIG 7
FIG 8

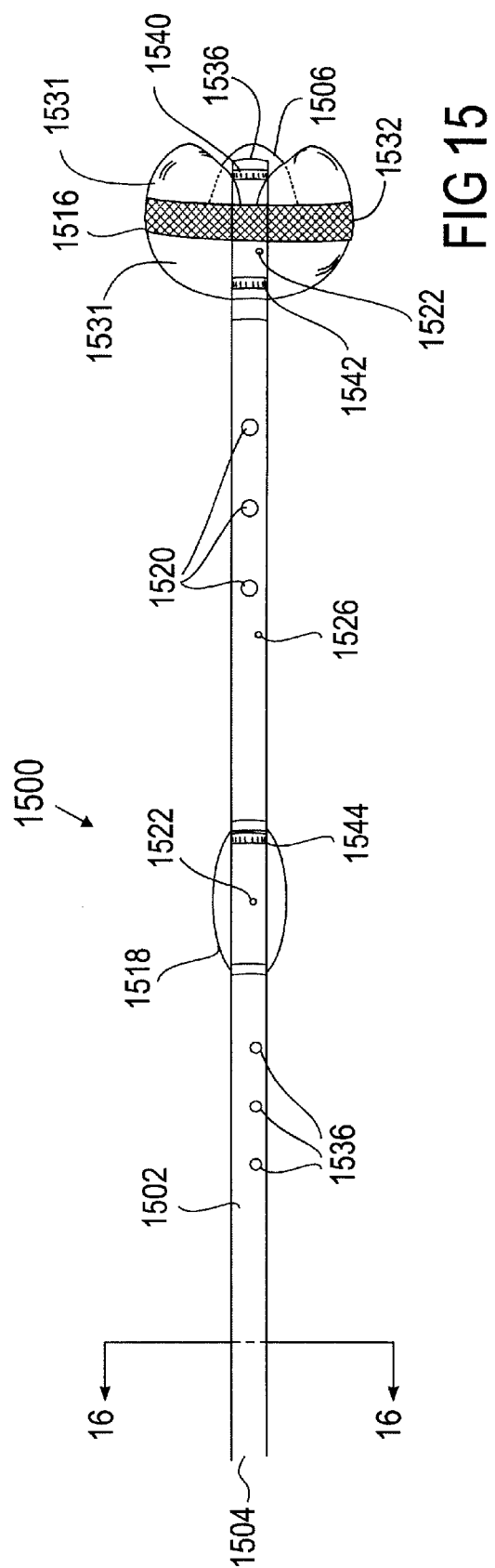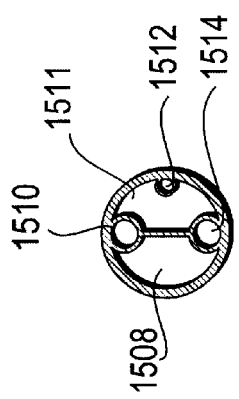

AORTIC CATHETER WITH POROUS AORTIC ROOT BALLOON AND METHODS FOR INDUCING CARDIOPLEGIC ARREST

This application claims benefit of Prov. No. 60/084,939 filed May 11, 1998.

FIELD OF THE INVENTION

The present invention relates generally to a system and methods for inducing cardioplegic arrest and for performing cardiopulmonary bypass procedures. More particularly, the invention relates to an aortic catheter having a porous aortic root balloon for controlling flow through the coronary arteries and the aortic lumen, and for inducing cardiac arrest. The invention further relates to devices for maintaining the competence of a patient's aortic valve and for preventing unwanted flow through the aortic valve.

BACKGROUND OF THE INVENTION

Recent advances in the field of minimally invasive cardiac surgery have included the development of aortic catheters and methods for inducing cardiac arrest without the necessity of opening the patient's chest with a sternotomy or other major thoracotomy. For example, U.S. Pat. No. RE 35,352 to Peters describes a single balloon catheter for occluding a patient's ascending aorta and a method for inducing cardioplegic arrest. A perfusion lumen or contralateral arterial cannula is provided for supplying oxygenated blood during cardiopulmonary bypass. U.S. Pat. No. 5,584,803 to Stevens et al. describes a single balloon catheter for inducing cardioplegic arrest and a system for providing cardiopulmonary support during closed chest cardiac surgery. A coaxial arterial cannula is provided for supplying oxygenated blood during cardiopulmonary bypass. The occlusion balloon of these catheters must be very carefully placed in the ascending aorta between the coronary arteries and the brachiocephalic artery, therefore the position of the catheter must be continuously monitored to avoid complications.

In clinical use, in patients with incompetent or regurgitant aortic valves, antegrade infusion of cardioplegia by aortic root injection is contraindicated because the pressure generated by infusion of cardioplegia overcomes the reduced competence of the valve, causing cardioplegia to enter the ventricle rather than entering the coronary arteries. In some cases the left ventricle may become distended. In patients with incompetent or regurgitant aortic valves, it is recommended that cardioplegia be administered by direct coronary cannulation or by retrograde perfusion through the coronary sinus. Direct coronary cannulation can be difficult and can dislodge plaques from ostial lesions in the coronary arteries. Retrograde perfusion of cardioplegia through the venous system has been used successfully, however, there is debate as to the effectiveness of this procedure, and correct placement of the catheters can be difficult. Furthermore, even in patients with normal aortic valves, pressures generated during surgery may cause the valve to become temporarily incompetent, leading to problems similar to those discussed above.

Another difficulty encountered with prior art aortic catheters is the tendency of the single balloon catheters to migrate or drift in the direction of the pressure gradient within the aorta. Specifically, during infusion of cardioplegia, the balloon catheter will tend to drift downstream away from the heart and toward the aortic arch and, while the cardiopulmonary bypass pump is on during the procedure and after completion of infusion of cardioplegia, the balloon catheter will tend to drift upstream in the opposite direction toward the heart into the aortic root. This migration can be problematic if the balloon drifts downstream far enough to occlude the brachiocephalic artery, or upstream enough to occlude the coronary arteries, or to pass through the aortic valve into the ventricle.

What is needed is a peripheral or central access catheter configuration that maintains the competence of weakened aortic valves, and does not challenge the competence of healthy aortic valves, during infusion of cardioplegia, and is more resistant than prior apparatus to migration due to pressure gradients within the patient's aorta.

The following patents are hereby incorporated herein in their entirety: U.S. Pat. Nos. 5,383,854, 5,308,320, 5,820,593 and 5,879,316 by Safar et al.; U.S. patent applications Ser. No. 08/909,293 filed Aug. 11, 1997, Ser. No. 08/909,380 filed Aug. 11, 1997 and Ser. No. 09/152,589 filed Sep. 11, 1998, by Safar et al.; U.S. Pat. No. 5,738,649 by John A. Macoviak; U.S. Pat. Nos. 5,827,237 and 5,833,671 by John A. Macoviak and Michael Ross; and U.S. patent application Ser. No. 08/665,635, filed Jun. 17, 1996, by John A. Macoviak and Michael Ross; U.S. patent application 09/205,753, filed Dec. 8, 1997, by Bresnahan et al.

SUMMARY OF THE INVENTION

Accordingly, the present invention provides an aortic catheter or cannula having a distal flow control member located at or near a distal end of the cannula. The distal flow control member is positioned within the aortic root and is intended to fulfill at least one and preferably all five of the following functions: occluding the aorta at the aortic root, perfusing the coronary arteries with a selected fluid, maintaining the competence of the aortic valve when perfusing the coronary arteries, resisting migration of the distal flow control member or cannula, and providing a bumper for tactile feedback when placing the catheter. Preferably, the distal flow control member may be an inflatable balloon that is inflated using a cardioplegia fluid, and which will occlude the aorta and deliver an effective volume of cardioplegia fluid to the coronary arteries. The distal flow control member may be shaped to conform to the shape of the aortic root and may also be shaped to conform to the cusps of the aortic valve. The material or materials used in the inflatable distal flow control member should have properties that allow an internal pressure within the distal flow control member to be maintained at a sufficient level to occlude the aorta, while also allowing a controlled volume of fluid to seep or otherwise escape from the balloon for perfusing the coronary arteries. Thus, the surface of the balloon may be porous, or have one or more porous regions, or include apertures that allow cardioplegia to seep or flow when a specific pressure is attained, and/or to prevent flow of cardioplegia when the pressure is higher or lower than ideal for coronary perfusion.

The catheter may further include one or more additional flow control members located downstream from the distal flow control member to segment the aorta for selective perfusion to different organ systems within the body. These flow control members may be inflatable balloons or selectively deployable external catheter valves. The catheter may further include one or more anchoring members located downstream from the distal flow control member. The downstream anchoring member may be a larger inflatable balloon or other anchoring structure that provides sufficient force or friction to prevent the catheter from drifting from a selected position within the aorta. Useable flow control members include, but are not limited to, expandable or inflatable members such as inflatable balloons and valves including collapsible/expandable valves of various configurations including retrograde valves, antegrade valves, and various central flow and peripheral flow valves.

A combination of valves and inflatable members may be used as appropriate for a given procedure, thus in some embodiments, the catheter body can include one or more antegrade and retrograde valves, as well as one or more inflatable balloons. Inflatable balloons and collapsible/deployable valves suitable for this application have been previously described in the patents incorporated by reference above and any desirable or practical inflatable balloon or deployable valve may be used. Inflatable balloons typically include an interior chamber that is in fluid communication with an inflation lumen extending within the catheter shaft a location from within the respective flow control member to a location in the proximal portion which is adapted to extend out of the patient.

A first embodiment of the aortic catheter system of the present invention is configured for retrograde deployment via a peripheral artery, such as the femoral artery. The aortic catheter has an elongated catheter shaft having a proximal end and a distal end. A distal flow control member, preferably in the form of an inflatable balloon, is mounted on the catheter shaft near the distal end of the catheter shaft so that it may be positioned within the aortic root when deployed. An inflation and cardioplegia lumen extends through the catheter shaft to one or more inflation ports within the distal flow control member. In the preferred embodiment, a guide wire lumen extends from the proximal end of the catheter shaft to the distal end of the shaft, and may have a hydrophilic or lubricious coating. Generally, the distal flow control member comprises an impermeable portion and a permeable portion. More exemplary embodiments will now be discussed.

In a second embodiment, the distal flow control member is a three-lobed balloon to conform to the shape of the aortic valve. In a third embodiment the distal flow control member is comprised of a balloon formed of a non-porous material, but having two or more porous windows that align with the coronary ostia for delivery of cardioplegia. In a fourth embodiment, the distal flow control member comprises a balloon comprising both a non-porous material portion, and a porous portion that extends circumferentially around the diameter of the balloon. In a fifth embodiment, bistable nipples or pressure valves are used. In a sixth embodiment, the distal flow control member comprises three adjacent balloons on the catheter shaft, with the most distal balloon conforming to the shape of the aortic valve, the middle balloon being porous, and the most proximal balloon being non-porous. In a seventh embodiment, a second balloon is positioned within a first outer balloon. When the inner balloon is fully inflated, the outer surface of the inner balloon contacts the inner surface of the outer balloon preventing escape of cardioplegia through the porous portions, nipples, or pressure valves located on the outer balloon. When the inner balloon is deflated, cardioplegia is allowed to flow. In an eighth embodiment, the distal flow control member comprises two adjacent balloons on the catheter shaft having porous surfaces facing each other.

In each embodiment discussed above, the distal flow control member preferably resists migration because the distal flow control member comprises a diameter larger than the diameter of the sinotubular ridge and the aortic valve annulus. In alternate embodiments, the surface of the flow control member may include a sticky polymer coating to further resist migration.

In a ninth embodiment of the invention, describes a catheter system for retrograde deployment that includes an additional occluding/anchoring member is described. In this configuration, the aortic catheter has an elongated catheter shaft having a proximal end and a distal end. Any of the previously described porous root balloons may be implemented. The porous aortic root balloon is mounted on the catheter shaft near the distal end of the catheter shaft so that it may be positioned within the aortic root when deployed and is capable of occlusion and cardioplegia delivery. An occluding/anchoring member, hereafter referred to as the anchoring member, in the form of an inflatable balloon, is mounted on the catheter shaft proximal to the porous root balloon and at a position located in the descending aorta when deployed. Preferably, an arch perfusion lumen extends through the catheter shaft from the proximal end to one or more arch perfusion ports on the exterior of the catheter shaft between the porous root balloon and the downstream anchoring member, to perfuse the aortic arch. An arch pressure lumen preferably extends through the catheter shaft from the proximal end to an arch pressure port located between the distal flow control member and the anchoring member to monitor pressure in the aortic arch. At least one inflation lumen extends through the catheter shaft from the proximal end to one or more balloon inflation ports located on the catheter shaft within the distal flow control member and the anchoring member. In other embodiments, each flow control member may be deployed using a separate lumen. A guide wire lumen extends from the proximal end of the catheter shaft to the distal end of the shaft. The distal flow control member used in this embodiment would be similar to the distal flow control member and alternative embodiments described previously. Occlusion of the aorta by the anchoring balloon may also be used to partition the aorta for differential perfusion of the partitioned portions.

In a tenth embodiment, otherwise similar to the ninth embodiment described above, the system performs the partitioning function of the anchoring balloon with a valve, which enables the partitioning of the aorta for differential perfusion.

Furthermore, methods according to the invention are described using the aortic catheter for occluding the ascending aorta at the aortic root and for perfusing a selected fluid to the coronary arteries and/or inducing cardioplegic arrest, for supporting the patient's circulation on cardiopulmonary bypass, for partitioning the patient's aorta and for performing selective aortic perfusion.

BRIEF DESCRIPTION OF THE DRAWINGS

FIG. 7 illustrates a third embodiment of the porous aortic root balloon perfusion catheter of the present invention configured for occluding the ascending aorta and delivering cardioplegia to the coronary ostia.

FIG. 8 illustrates a fourth embodiment of the porous aortic root balloon perfusion catheter of the present invention configured for occluding the ascending aorta and delivering cardioplegia to the coronary ostia.

FIG. 15 illustrates a shaft portion of the catheter system configured for insertion into a peripheral artery, such as the femoral artery, capable of occluding the ascending aorta, delivering cardioplegia to the coronary ostia and providing differential perfusion.

FIG. 16 illustrates a magnified lateral cross portion of the aortic catheter of FIG. 15 taken along line 16—16 illustrating the multilumen arrangement of the catheter shaft.

DETAILED DESCRIPTION

The porous aortic root balloon perfusion catheter of the present invention generally comprises a catheter shaft configured for peripheral artery access or central artery access, having sufficient length to reach from an insertion site to the ascending aorta and a distal flow control member, in the form of a porous aortic root member, which is configured to deliver cardioplegia to the coronary ostia and is also capable of substantially occluding the ascending aorta. With the aforementioned general features in mind, the following illustrative embodiments will show in greater detail the specific aspects of the present invention.

FIGS. 1–4 are marked with parallel series of reference numbers. Like features are identified by a two-digit reference number preceded by a prefix identifying the drawings figure where the feature appears. Features that are not explicitly described in the specification can be identified by reference to the other figure descriptions in this grouping.

Figure 1:
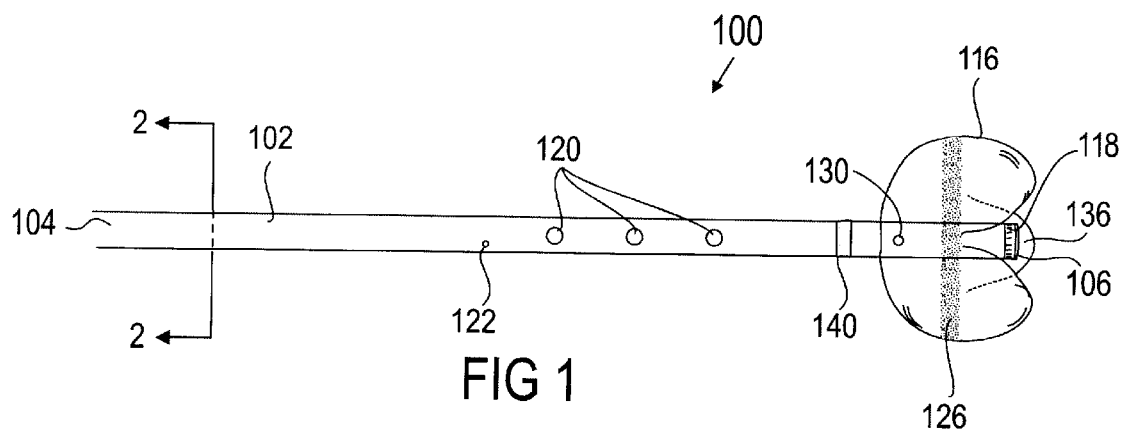
FIG. 1 illustrates a shaft portion of a first embodiment of the porous aortic root balloon perfusion catheter of the present invention configured for insertion into a peripheral artery and configured to occlude the ascending aorta and deliver cardioplegia to the coronary ostia.

FIG. 1 illustrates a shaft portion of a first embodiment of the porous aortic root balloon perfusion catheter of the present invention configured for insertion into a peripheral artery, such as the femoral artery, and capable of both occluding the ascending aorta and delivering cardioplegia to the coronary ostia. The porous aortic root balloon catheter 100 has an elongated catheter shaft 102 having a proximal end 104 and a distal end 106. Preferably, the elongated catheter shaft 102 has an outer diameter which is from approximately 9 to 22 French (3.0–7.3 mm diameter), more preferably from approximately 12 to 18 French (4.0–6.0 mm diameter), and an overall length from approximately 60 to 120 cm, more preferably 70 to 90 cm, for femoral artery deployment in adult human patients. The catheter shaft 102 is preferably formed of a flexible thermoplastic material, a thermoplastic elastomer, or a thermoset elastomer. Suitable materials for use in the elongated catheter include, but are not limited to, polyvinylchloride, polyurethane, polyethylene, polyamides, polyesters, silicone, latex, and alloys or copolymers thereof, as well as braided, coiled or counterwound wire or filament reinforced composites.

A distal flow control member 116, in this illustrative embodiment in the form of an inflatable porous root balloon, is mounted on the catheter shaft 102 near the distal end 106 by heat welding or with an adhesive. The inflatable porous root balloon 116 has a deflated state in which the diameter of the porous root balloon 116 is, preferably, not substantially larger than the diameter of the catheter shaft 102, and an inflated state in which the porous root balloon 116 expands to a diameter sufficient to occlude blood flow in the aortic root of the patient. For use in adult humans, the distal flow control member 116 preferably has an inflated outer diameter of approximately 2 to 5 cm. The catheter shaft 102 is navigated transluminally into the ascending aorta until the porous root balloon 116 is capable of delivering cardioplegia through a porous material 126 to the coronary ostia and is also capable of substantially occluding the ascending aorta when deployed. The material or materials used in the porous root balloon 116 are preferably characterized by properties that allow an internal pressure within the distal flow control member to be maintained at a sufficient level to occlude the aorta, while also allowing a controlled volume of fluid to escape from the flow control member for perfusing the coronary arteries. Thus, the surface of the balloon may be porous, or have porous regions, or include apertures that allow cardioplegia to seep or flow at a known rate when a specific pressure is attained.

Figure 2:
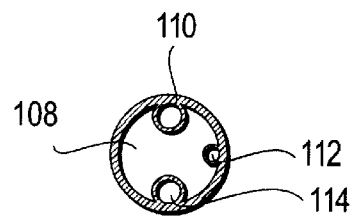
FIG. 2 illustrates a magnified lateral cross portion of the aortic catheter of FIG. 1 taken along line 2–2.

As shown in FIG. 2, which is a magnified lateral cross portion of the aortic catheter 100 of FIG. 1 taken along line 2—2, the catheter shaft 102 has four lumens: a perfusion lumen 108, a pressure lumen 112, an inflation cardioplegia lumen 110, and a guide wire lumen 114. The configuration of the lumens shown is for illustrative purposes only, and other configurations could be used. For example, in alternate embodiments the catheter shaft 102 may not include a perfusion lumen 108 and a separate arterial perfusion cannula would be provided which would simplify the overall construction of the aortic catheter 100. In these alternative embodiments, which can be used for all embodiments described herein, a separate integral or nonintegral slidably disposed coaxial arterial cannula may be used. Alternatively, a contralateral or collateral arterial cannula can be provided. In the case of a contralateral arterial cannula insertion into the other femoral artery may necessary. Referring now to FIGS. 1 and 2 the perfusion lumen 108 extends through the catheter shaft 102 from the proximal end 104 to one or more perfusion ports 120 on the exterior of the catheter shaft 102 proximal to the distal flow control member 116. The pressure lumen 112 extends through the catheter shaft 102 from the proximal end 104 to a pressure port 122 located proximal to the distal flow control member 116 to monitor pressure near the aortic arch. The inflation/cardioplegia lumen 110 extends through the catheter shaft 102 from the proximal end 104 to an inflation/cardioplegia port 130 for inflation and deflation of the distal flow control member 116 with cardioplegia fluid. The guide wire lumen 114 extends from the proximal end 104 of the catheter shaft 102 to a guide wire port 136 at the distal end 106 of the catheter shaft 102, distal to the distal flow control member 116. Attached to the proximal end 104 of the catheter shaft 102 is a manifold 350 with fittings for each of the catheter lumens, which shall be described in more detail below in connection with FIG. 3. The aortic catheter 100 includes a distal radiopaque marker 118 positioned near the distal end 106 of the catheter shaft 102, and a proximal radiopaque marker 140 positioned near the proximal edge of the distal flow control member 116.

Figure 3:
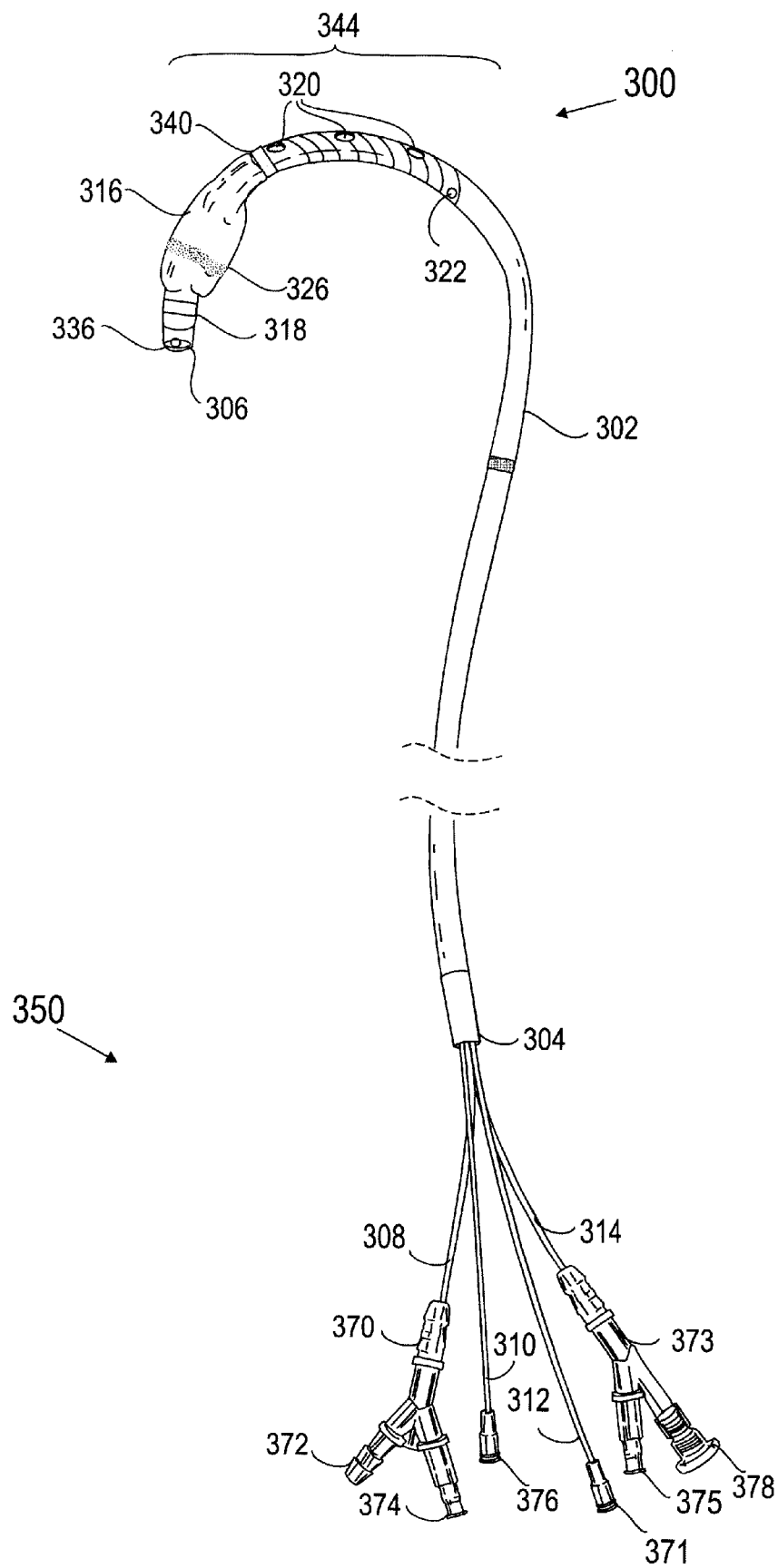
FIG. 3 shows a side view of an aortic catheter according to the present invention with a catheter shaft configured for retrograde deployment via femoral artery access.

FIG. 3 shows a side view of an aortic catheter 300 according to the present invention with a catheter shaft 302 configured for retrograde deployment via femoral artery access. In order to facilitate placement of the aortic catheter 300 and to improve the stability of the catheter 300 in the proper position in the patient's aorta, a distal region 344 of the catheter shaft 302 may be preshaped with a curve to match the internal curvature of the patient's aortic arch. The curved distal region 344 represents a J-shaped curve of approximately 180 degrees of arc with a radius of curvature of approximately 2 to 4 cm to match the typical curvature of the aortic arch in an adult human patient. In addition, the distal end 306 of the catheter may be skewed slightly up out of the plane of the curve to accommodate the forward angulation of the patient's ascending aorta. Additionally, the catheter shaft 302 may be reinforced, particularly in the curved distal region 344, for example with braided or coiled wire, to further improve the stability of the catheter 300 in the proper position in the patient's aorta. The elongated catheter shaft 302 is preferably formed of a flexible thermoplastic material, a thermoplastic elastomer, or a thermoset elastomer. Suitable materials for use in the elongated catheter include, but are not limited to, polyvinylchloride, polyurethane, polyethylene, polyamides, polyesters, silicone, latex, and alloys or copolymers thereof, as well as braided, coiled or counterwound wire or filament reinforced composites.

As mentioned above, the proximal end 304 of the catheter shaft 302 is connected to a manifold 350 with fittings for each of the catheter lumens. The corporeal perfusion lumen 308 is connected to a Y-fitting 370 that has a barb connector 372 for connection to a perfusion pump or the like and a luer connector 374, which may be used for monitoring perfusion pressure, for withdrawing fluid samples or for injecting medications or other fluids. The pressure lumen 312 is connected to a luer connector 371 or other fitting suitable for connection to a pressure monitor. The inflation/cardioplegia lumen 310 is connected to a luer connector 376 or other fitting suitable for connection to a cardioplegia source. The guide wire lumen 314 is connected to a Y-fitting 373 that has a luer connector 375 and a guide wire port 378 with a Touhy-Borst adapter or other hemostasis valve. Alternatively, a second perfusion lumen may be added with perfusion ports located downstream from the perfusion ports 320 for separately perfusing the corporeal body. In addition, a separate coaxial, collateral or contralateral arterial cannula may be implemented to perfuse the corporeal body in a retrograde direction separate from the perfusion lumen 308 to minimize the catheter shaft outer diameter.

Figure 4:
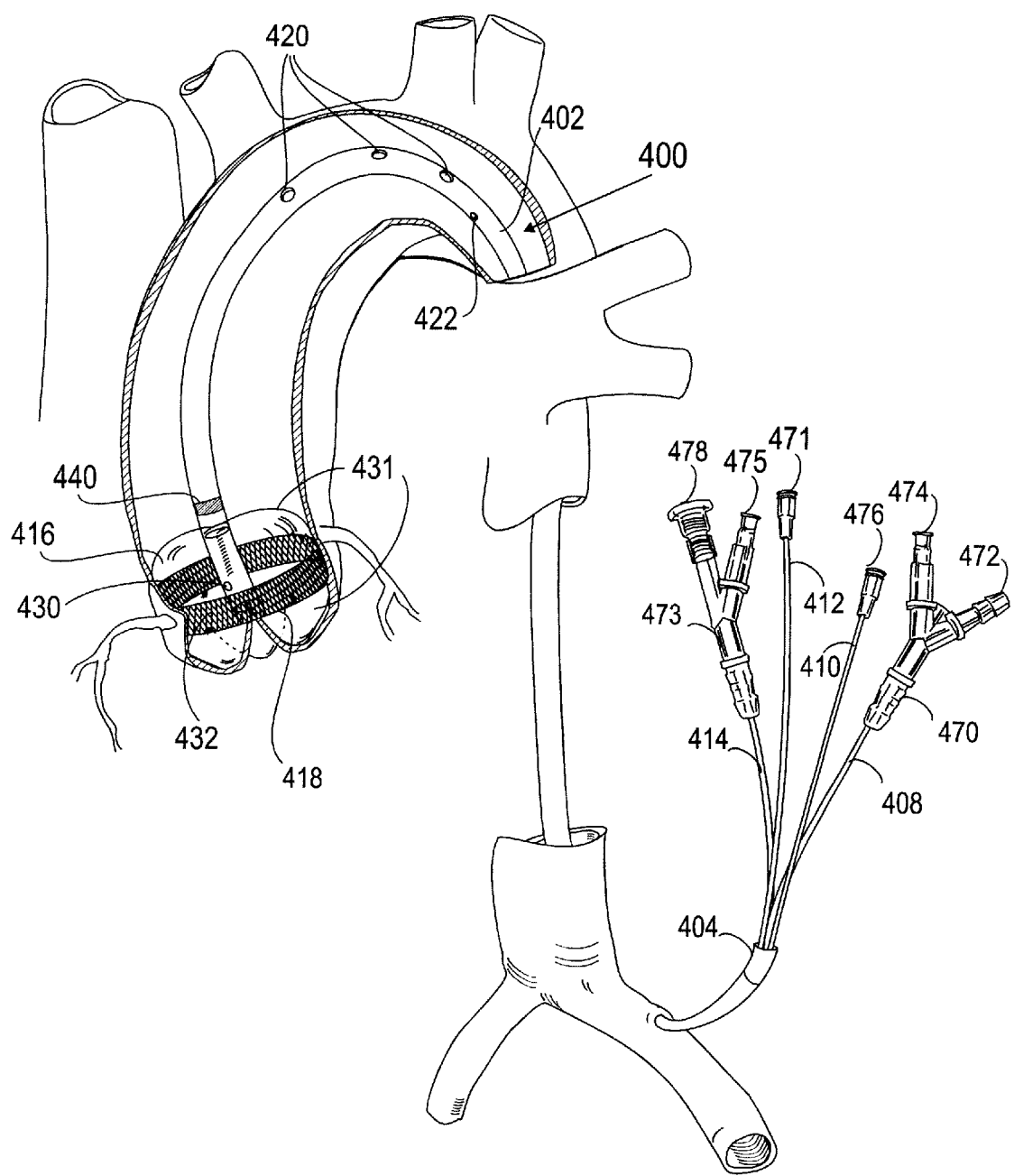
FIG. 4 is a schematic diagram showing an aortic catheter according to the present invention deployed within a patient's aorta via femoral artery access.

FIG. 4 is a schematic diagram showing an aortic catheter 400 according to the present invention deployed within a patient's aorta via femoral artery access. The aortic catheter 400 is introduced into the patient's circulatory system through a peripheral artery access, such as the femoral artery, by using the percutaneous Seldinger technique, through an introducer sheath or via an arterial cutdown. The catheter 400 may optionally be introduced into the femoral artery through a coaxial arterial perfusion cannula (not shown). Meanwhile, one or more venous cannulae are introduced into the vena cava via the femoral vein or the jugular vein. The aortic catheter 400 is advanced up the descending aorta and across the aortic arch under fluoroscopic or ultrasound guidance with the aid of a guide wire within the guide wire lumen 414. The aortic catheter 400 is advanced until the distal flow control member 416, in this illustrative embodiment in the form of a porous aortic root balloon, is positioned within the ascending aorta within the aortic root. The distal flow control member 416 may be partially inflated enabling the distal flow control member 416 to serve as an atraumatic bumper giving tactile feedback when the catheter has touched the aortic valve. In addition, the radiopaque markers 418 and 440 can be referenced to establish proper placement of the distal flow control member 416. Once proper placement is established, the guide wire is withdrawn.

Using a multihead cardiopulmonary bypass pump or the like, perfusion of oxygenated blood is started through the perfusion ports 420 (or arterial cannula). The distal flow control member 416 is totally inflated with a cardioplegia solution to partition the aorta, whereupon a cardioplegic agent, such an cold crystalloid cardioplegia or blood cardioplegia, is infused through the distal flow control member 416 to induce cardioplegic arrest. Generally, the distal flow control member 416 will have an inflated diameter sufficient to occlude blood flow through the aortic root. Since the diameter of the aortic root is typically somewhat larger than the diameter of the ascending aorta, the fully inflated distal flow control member 416 is prevented from leaving the aortic root by the sinotubular ridge and the aortic valve annulus.

Typically, during surgery, approximately 500 ml to 1,000 ml of cardioplegia is infused to the heart at an initial rate of 250 ml to 350 ml/minute to induce cardioplegic arrest. The flow is then typically continued intermittently, alternating between no flow of cardioplegia and a low flow of cardioplegia ranging from 25 to 250 ml/minute, to prevent the heart from resuming a sinus rhythm until the operation is complete. Therefore, it is preferable that the flow rate of cardioplegia be controllable within a range from 0 ml to 500 ml/minute, and more preferably within a range from 0 ml to 350 ml/minute. Alternatively, an initial bolus of cardioplegia may be delivered by other known means such as direct injection into the aortic root or into the coronary arteries, a separate coronary sinus catheter, or other known means for infusing cardioplegia, then a lower maintaining quantity of cardioplegia is infused using the aortic catheter of the invention.

Figure 5:
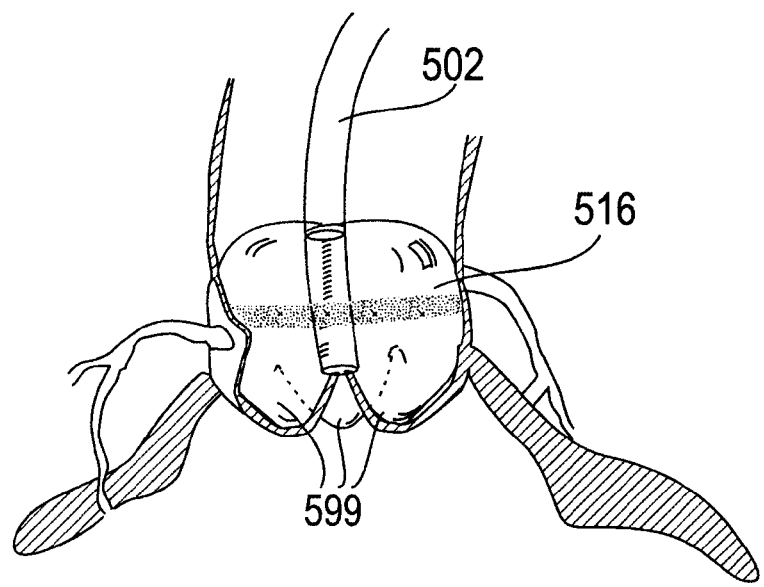
FIG. 5 illustrates is a second embodiment of the present invention illustrating a three-lobed porous aortic root balloon positioned within an aortic root, configured to conform to the shape of the cusps of the aortic valve when deployed.
Figure 6:
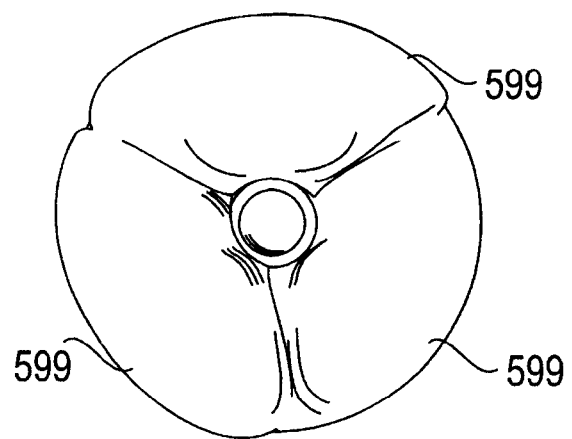
FIG. 6 is a distal end view of the porous aortic root balloon of FIG. 5 illustrating the three-lobed configuration.

In one illustrative embodiment, the distal flow control member 416 is shaped to conform somewhat to the shape of the aortic root, and may further conform to the shape of the aortic valve. Illustrated in FIG. 5 is a second embodiment of the present invention illustrating a three-lobed porous aortic root balloon 516 positioned within an aortic root, configured to conform to the shape of the cusps of the aortic valve when deployed. The lengths of the lobes 599 of the porous aortic root balloon 516 are aligned longitudinally with respect to the catheter shaft 502 and the aortic valve. FIG. 6 is a distal end view of the porous aortic root balloon 516 of FIG. 5 taken along line 6—6 illustrating the three-lobed configuration. The lobes 599 are configured to support the cusps of the aortic valve and maintain the competence of the aortic valve against pressure in the aortic lumen. The three-lobed balloon embodiment can be easily incorporated into this or any embodiment disclosed herein. Alternatively, the distal flow control member 416 may be compliant, or formed of a compliant material so that the inflated balloon conforms to the shape of the aortic valve when inflated.

Referring back to FIG. 4, the distal flow control member 416 is comprised of a non-porous portion 431 where cardioplegic fluid is not allowed to seep therethrough and a porous portion 432 where cardioplegic solution is allowed to seep therethrough. The size, shape, and position of the porous portion 432, as shown, is for illustrative purposes only, any other desired sizes, shapes, or positions may be used. The porous portion 432 and non-porous portion 431 of the porous aortic root balloon 416 may be formed from the same or separate materials. Suitable materials for the non-porous portions 431 of the distal flow control member 416 include, but are not limited to, elastomers, thermoplastic elastomers, polyvinylchloride, polyurethane, polyethylene, polyamides, polyesters, silicone, latex, and alloys or copolymers and reinforced composites thereof. In addition, the outer surface of the distal flow control member 416 may include a force or friction increasing means such as a friction increasing coating or texture to increase friction between the distal flow control member 416 and the aortic wall when deployed. Suitable materials for the porous portion 432 include, but are not limited to, a perforated polymer film, porous or microporous membranes, TYVEK (spun-bonded polyethylene), expanded PTFE (GORTEX), woven or knit mesh or fabric, or the like.

A selected fluid, such as a cardioplegia fluid, is introduced into the distal flow control member 416 by way of the inflation/cardioplegia lumen 410. Any acceptable cardioplegia fluid may be used, such as cold crystalloid cardioplegia, normothermic blood cardioplegia, or hypothermic blood cardioplegia. In an alternate embodiment, it may be preferable to prime the balloon with a more viscous solution, for example a radiopaque contrast agent mixed with saline solution or with cardioplegic solution to initially inflate the balloon with a solution that will leak from the balloon at a rate slower than the cardioplegia solution will leak. When the distal flow control member 416 is fully inflated, the porous portion 432 should be positioned over the coronary ostia. It is possible, but uncommon, for a heart to have more than two coronary ostia. The number and positioning of the porous portion 432 may be selected to compensate for this or other unusual anatomical arrangements. When the correct pressure is attained, the member 416 occludes blood flow through the aortic lumen. The cardioplegia fluid used to inflate the distal flow control member 416 seeps through the porous portion 432 at a known rate into the coronary arteries. The flow rate may be adjustable by adjusting the pressure within the distal flow control member 416. The competence of the aortic valve is not challenged because the cardioplegic fluid is delivered directly to the coronary arteries, thus preferably; the aortic valve does not experience significant retrograde fluid pressure. The distal flow control member 416 prevents seepage of cardioplegia fluid through the porous portion 432 by contacting the aortic wall with portions of porous windows 432 not aligned with the coronary ostia. Preferably, only the areas in contact with the coronary ostia are capable of delivering cardioplegia since this is the only area with an open space for the fluid to travel.

Perfusion of the patient is maintained through the perfusion ports 420 (and/or arterial cannula) and cardioplegic arrest is maintained by continued infusion of the cardioplegic agent through the distal flow control member 416 for as long as necessary for completion of the surgical procedure using minimally invasive or standard open-chest techniques. At the completion of the surgical procedure, the distal flow control member 416 is deflated to allow oxygenated blood to flow into the patient's coronary arteries, whereupon the heart should spontaneously resume normal sinus rhythm. If necessary, cardioversion or defibrillation shocks may be applied to restart the heart. The patient is then weaned off of bypass and the aortic catheter 400 and any other cannulae are withdrawn.

FIG. 7 illustrates a third embodiment of the porous aortic root balloon perfusion catheter of the present invention configured for occluding the ascending aorta and delivering cardioplegia to the coronary ostia. The distal flow control member in this third embodiment is in the form of a porous aortic root balloon 716 having a non-porous material portion 733 surrounding one or more porous windows 730. The size, shape, and position of the porous windows 730 are shown for illustrative purposes, and any other desired sizes, shapes, or positions may be used. The porous windows 730 and non-porous 733 portions may be formed from the same or separate materials. Suitable materials for the non-porous 733 portion of the porous aortic root balloon 716 include, but are not limited to, elastomers, thermoplastic elastomers, polyvinylchloride, polyurethane, polyethylene, polyamides, polyesters, silicone, latex, and alloys or copolymers and reinforced composites thereof. In addition, the outer surface of the porous aortic root balloon 716 may include a force or friction increasing means such as a friction increasing coating or texture to increase friction between the porous aortic root balloon 716 and the aortic wall when deployed. Suitable materials for the porous windows 730 include, but are not limited to, a perforated polymer film, porous or microporous membranes, TYVEK (spun-bonded polyethylene), expanded PTFE (GORTEX), woven or knit mesh or fabric, or the like.

In use, the porous aortic root balloon 716 is positioned within the aortic root. A selected fluid, such as a cardioplegia fluid, is introduced through the inflation/cardioplegia lumen 710 into the inflatable distal flow control member 716. Any acceptable cardioplegia fluid may be used, such as cold crystalloid cardioplegia, normothermic blood cardioplegia, or hypothermic blood cardioplegia. Some cardioplegia fluid may seep out through the porous windows 730 during inflation, but at a rate less than the rate at which the cardioplegia enters porous aortic root balloon 716. In an alternate embodiment, it may be preferable to prime the balloon with a more viscous solution, for example a radiopaque contrast agent mixed with saline solution or with cardioplegic solution, that is, to initially inflate the balloon with a solution that will leak from the balloon at a rate slower than the cardioplegia solution will leak. When the porous aortic root balloon 716 is fully inflated, at least one porous window 730 should be positioned over the opening of each coronary ostium. It is possible, but uncommon, for a heart to have more than two coronary ostia. The number and positioning of the porous windows 730 may be selected to compensate for this or other unusual anatomical arrangements.

When the correct pressure is attained, the porous aortic root balloon 716 occludes blood flow through the aortic lumen. Concurrently the cardioplegia fluid used to inflate the porous aortic root balloon 716 escapes through the porous windows 730 at certain predetermined pressures and at a known rate of flow into the coronary arteries. The flow rate may be adjustable by adjusting the pressure within the porous aortic root balloon 716. The competence of the aortic valve is not challenged because the cardioplegic fluid is delivered directly to the coronary arteries, thus preferably, the aortic valve does not experience significant retrograde fluid pressure. The contact of the wall of the porous aortic root balloon 716 against the aortic wall prevents seepage of cardioplegia fluid through the porous windows 730 or the portions of porous windows 730 not aligned with the coronary ostia.

FIG. 8 illustrates a fourth embodiment of the porous aortic root balloon perfusion catheter of the present invention configured for occluding the ascending aorta and delivering cardioplegia to the coronary ostia. However, rather than separate porous windows, a large, preferably circumferential, porous strip or patch 832 is used instead of the porous windows of the previous embodiment. The size and position of the porous strip 832 is shown in FIG. 8 for illustrative purposes only, and other configurations may be used. The width and position of the porous strip 832 is preferably chosen to cover the coronary ostia of the typical patient. One advantage to the larger porous area is that the porous root balloon 816 need not be as carefully positioned to assure the alignment of the porous portion with each coronary ostium. The porous 832 and non-porous 833 portions of the distal flow control member 816 may be made from the same or different materials. Suitable materials for the non-porous portions 833 of the porous aortic root balloon 816 include, but are not limited to, elastomers, thermoplastic elastomers, polyvinylchloride, polyurethane, polyethylene, polyamides, polyesters, silicone, latex, and alloys or copolymers and reinforced composites thereof. In addition, the outer surface of the distal flow control member 816 may include a friction increasing means such as a friction increasing coating or texture to increase friction between the porous aortic root balloon 816 and the aortic wall when deployed. Suitable materials for the porous strip 832 include but are not limited to a perforated polymer film, porous or microporous membranes, TYVEK (spun-bonded polyethylene), expanded PTFE (GORTEX), woven or knit mesh or fabric, or the like.

In use, the porous aortic root balloon 816 is positioned within the aortic root. A cardioplegia fluid is introduced to the porous aortic root balloon 816 through the inflation/cardioplegia lumen 810 into the porous aortic root balloon 816. As previously described, any acceptable cardioplegia fluid may be used. Some cardioplegia fluid may seep from the porous strip 832 during inflation, but at a rate less than the rate at which the cardioplegia enters the porous aortic root balloon 816. When the porous aortic root balloon 816 is fully inflated, the porous strip 832 should be positioned so that some portion of the porous strip 832 covers each coronary ostium. When the correct pressure is attained, the porous aortic root balloon 816 occludes blood flow through the aortic lumen. The cardioplegia fluid used to inflate the distal flow control member escapes through the porous strip 832 where the porous strip 832 covers the coronary ostia, at a known rate. Contact between the wall of the porous aortic root balloon 816 and the aortic wall prevents seepage of cardioplegia fluid through portions of the porous strip 832 not aligned with a coronary ostium. The flow rate may be adjustable by adjusting the pressure within the porous aortic root balloon 816. The competence of the aortic valve is not challenged because the cardioplegic fluid is delivered directly to the coronary arteries.

Figure 9:
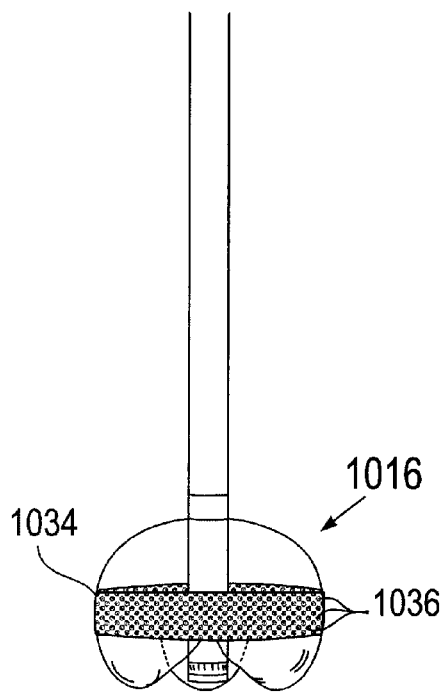
FIG. 9 illustrate a fifth embodiment of the porous aortic root balloon perfusion catheter of the present invention configured for occluding the ascending aorta and delivering cardioplegia to the coronary ostia having a circumferential region covered with bistable nipples.
Figure 10:
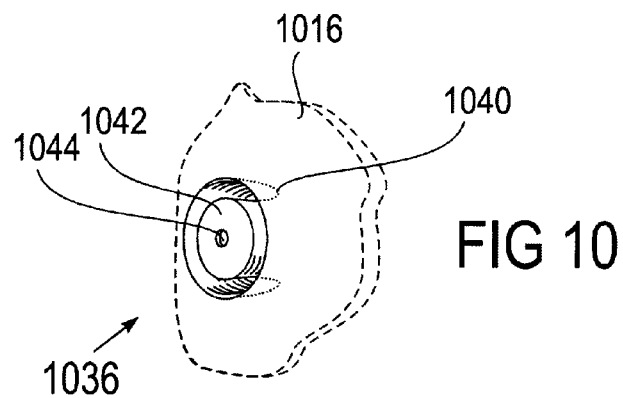
FIG. 10 illustrates a magnified view of an exemplary design of a single bistable nipple in an inverted low pressure configuration wherein low or no flow of cardioplegia is permitted.
Figure 11:
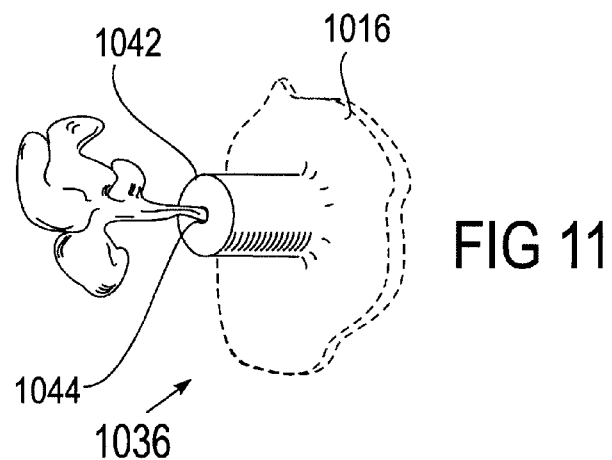
FIG. 11 illustrates a magnified view of an exemplary design of a single bistable nipple in the everted high pressure configuration wherein flow of cardioplegia is permitted.

FIGS. 9 through 11 collectively illustrate a fifth embodiment of the porous aortic root balloon perfusion catheter of the present invention configured for occluding the ascending aorta and delivering cardioplegia to the coronay ostia having a circumferential region 1034 covered with bistable nipples 1036. In any of the embodiments described above, the porous portions may be replaced by portions having bistable nipples, pressure valves, micropores, micro-nipples or the like. FIG. 10 illustrates a magnified view of an exemplary design of a single bistable nipple 1036 in an inverted low pressure configuration wherein low or no flow of cardioplegia is permitted. FIG. 11 illustrates a magnified view of an exemplary design of a single bistable nipple 1036 in the everted high pressure configuration wherein flow of cardioplegia is permitted. The nipple 1036 comprises a cylinder 1040 resting in a cylindrical fold, and a top surface 1042 having a pressure valve aperture 1044 located in the center of the top surface 1042. The nipple 1036 may be formed so that, in the low pressure configuration, forces exerted around the circumference of the top surface 1042 by the cylindrical fold tend to compress the top surface 1042, closing the pressure valve aperture 1044. The valve aperture 1044 may be in the form of a hole, a slit, or a cross slit in the top surface 1042. Preferably, the nipple 1036 will maintain this configuration at pressures existing in the porous aortic root balloon 1016 when inflated for occlusion of the aortic root. However, when the pressure is increased beyond a predetermined level, the nipple everts, as seen in FIG. 11. The folded portion unfolds as the nipple top 1042 moves outward from the distal flow control member 1216 outer surface. The pressure around the nipple top 1042 caused by the circumferential fold is released, and the aperture 1044 opens, allowing cardioplegia fluid flow. Contact of the nipple top 1042 with the aortic root wall at portions of the balloon not over the coronary ostia prevents the bistable nipples 1036 from everting and allowing significant cardioplegia fluid flow. In alternate embodiments, other known pressure valves or nipples may be used.

The porous aortic root balloon 1016 having nipple or pressure valves may be fabricated from a single material, or different materials may be used in the portions containing nipples or pressure valves and those regions which do not contain nipples or pressure valves. Suitable materials include, but are not limited to, elastomers, thermoplastic elastomers, polyvinylchloride, polyurethane, polyethylene, polyamides, polyesters, silicone, latex, and alloys or copolymers and reinforced composites thereof.

In any of the embodiments described above, the porous aortic root balloon 1016 may be configured as shown in FIGS. 5 and 6, which discloses a three-lobed balloon embodiment of the distal flow control member 516 positioned within an aortic root, shaped to conform to the shape of the cusps of the aortic valve when properly deployed. The lobes are configured to support the cusps of the aortic valve and maintain the competence of the aortic valve against pressure in the aortic lumen. The three-lobed balloon embodiment works in the same manner as any of the previously described embodiments including porous membranes or nipples. The same materials used in previous embodiments may be used in construction of this embodiment.

Figure 12:
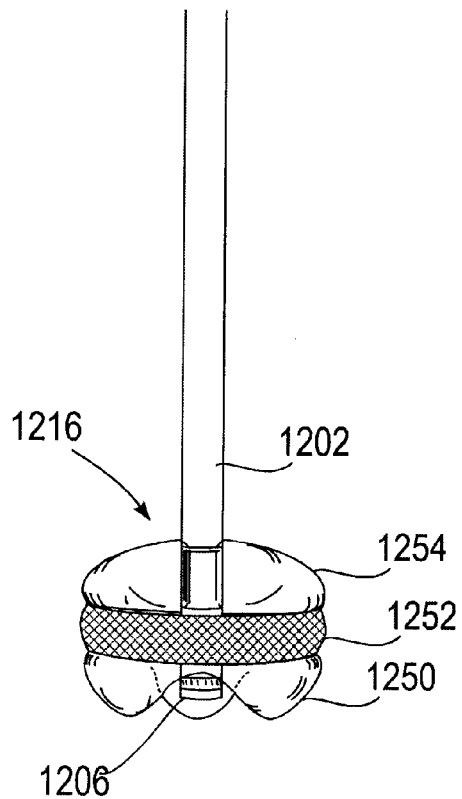
FIG. 12 illustrates a sixth embodiment of the porous aortic root balloon perfusion catheter of the present invention configured for occluding the ascending aorta and delivering cardioplegia to the coronary ostia.

FIG. 12 illustrates a sixth embodiment of the porous aortic root balloon perfusion catheter of the present invention configured for occluding the ascending aorta and delivering cardioplegia to the coronary ostia. In this illustrative embodiment, the distal flow control member is comprised of a first occlusion balloon 1250, a second porous balloon 1252, and a third occlusion balloon 1254. The first occlusion balloon 1250, located nearest the distal end 1206 of the aortic catheter shaft 1202, is preferably comprised of a non-porous material, and is preferably configured to conform to the cusps of the aortic valve. The first occlusion balloon 1250 is intended to prevent cardioplegia from entering the ventricle through the aortic valve. The second porous balloon 1252 is positioned adjacent the proximal side of the first occlusion balloon 1250. The second porous balloon 1252 is preferably formed of a porous material, or includes other means for allowing a controlled amount of cardioplegia to escape. The third occlusion balloon 1254 is located adjacent the second porous balloon 1252. The purpose of this balloon is primarily for occluding the aorta to prevent cardioplegia from entering the aortic arch. The third occlusion balloon 1254 is preferably comprised of a non-porous material, and is shaped to conform to the top of the aortic root.

Figure 13:
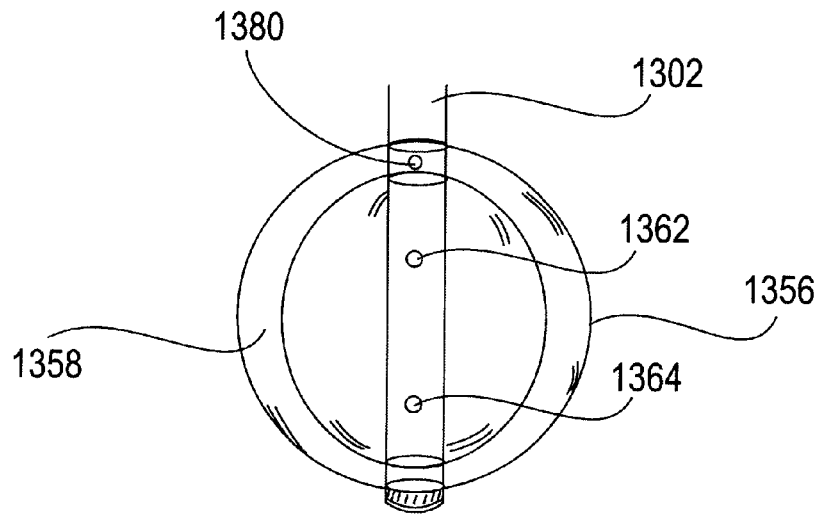
FIG. 13 illustrates a seventh embodiment of the porous aortic root balloon perfusion catheter of the present invention configured for occluding the ascending aorta and delivering cardioplegia to the coronary ostia.

FIG. 13 illustrates a seventh embodiment of the porous aortic root balloon perfusion catheter of the present invention configured for occluding the ascending aorta and delivering cardioplegia to the coronary ostia. In this illustrative embodiment, the distal flow control member on catheter shaft 1302 is comprised of a first outer balloon 1356 and a second inner balloon 1358 is positioned therein. The first outer balloon 1356 includes porous portions comprising porous material, nipples, or valves, to allow a controlled flow of cardioplegia. The second inner balloon 1358 is preferably nonporous. When the second inner balloon 1358 is fully inflated, the outer surface of the second inner balloon 1358 contacts the inner surface of the first outer balloon 1356, preventing escape of cardioplegia through the porous portions, nipples, or pressure valves located on the first outer balloon 1356. When the first inner balloon 1358 is fully or partially deflated, cardioplegia flow is allowed to resume. Separate lumens connecting to the outer balloon port 1380 and the inner balloon ports 1364 and 1362 are required for independently inflating the first outer balloon 1356 and the second inner balloon 1358.

Figure 14:
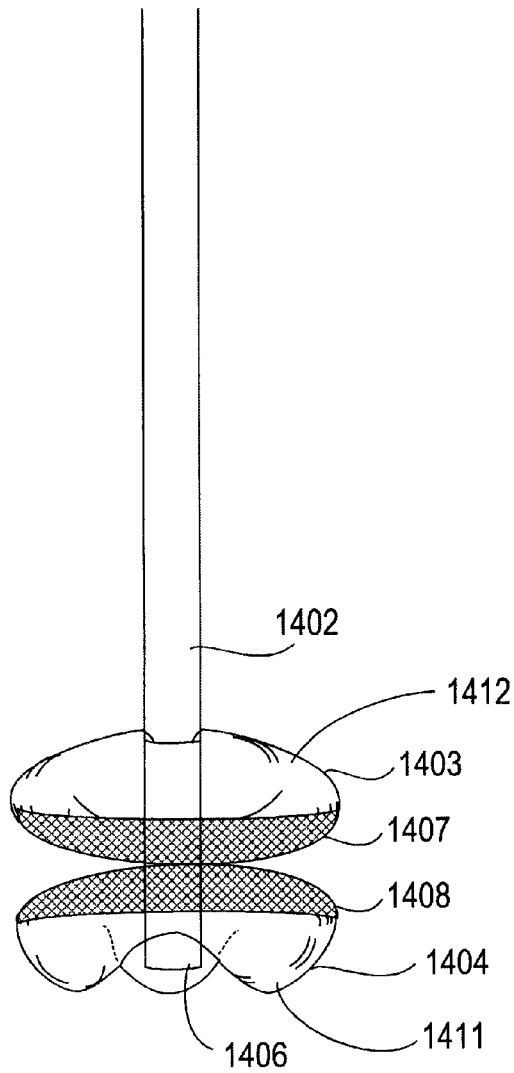
FIGS. 14 and 14a illustrate an eighth embodiment of the porous aortic root balloon perfusion catheter of the present invention configured for occluding the ascending aorta and delivering cardioplegia to the coronary ostia.
Figure 14A:
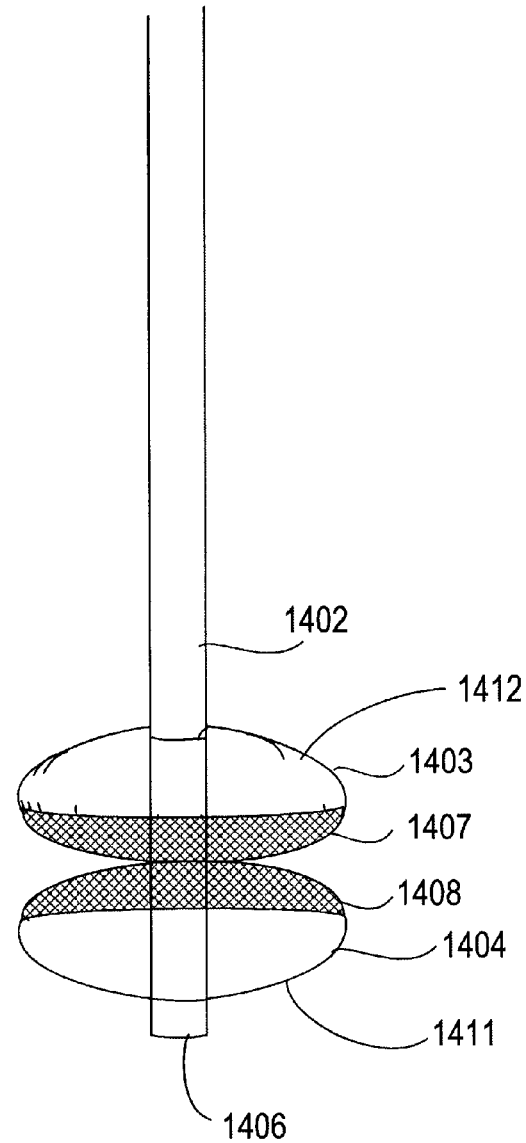

FIGS. 14 and 14a illustrate an eighth embodiment of the porous aortic root balloon perfusion catheter of the present invention configured for occluding the ascending aorta and delivering cardioplegia to the coronary ostia. In this illustrative embodiment, the distal flow control member is comprised of two adjacent occlusion balloons 1403 and 1404. The first occlusion balloon 1404, located nearest the distal end 1406 of the aortic catheter shaft 1402, preferably comprises a hemispherical nonporous portion 1411, and a hemispherical porous portion 1408 located on the proximal side of the first occlusion balloon 1404. As shown in FIGS. 14 and 14a the first occlusion balloon 1404 may have at least one lobe for biasing an aortic valve leaflet. The second balloon 1403 is positioned adjacent the proximal side of the first occlusion balloon 1404, and preferably comprises a hemispherical non-porous portion 1412 and a hemispherical porous portion 1407 located on the proximal side of the second occlusion balloon 1403. Alternatively, only one of the balloons 1403 or 1404 may include a porous portion.

FIGS. 15–19 are marked with parallel series of reference numbers. Like features are identified by a two-digit reference number preceded by a prefix identifying the drawing figure where the feature appears. Features that are not explicitly described in the specification can be identified by reference to the other figure description in this grouping.

FIGS. 15 and 16 illustrate a ninth embodiment of the porous aortic root balloon perfusion catheter system of the present invention configured for insertion into a peripheral artery and having a downstream anchoring member to stabilize the catheter shaft. FIG. 15 illustrates a shaft portion of the catheter system configured for insertion into a peripheral artery, such as the femoral artery, capable of occluding the ascending aorta, delivering cardioplegia to the coronary ostia and providing differential perfusion. A porous aortic root balloon catheter 1500 has an elongated catheter shaft 1502 having a proximal end 1504 and a distal end 1506. Preferably, the elongated catheter shaft 1502 has an outer diameter which is from approximately 9 to 22 French (3.0–7.3 mm diameter), more preferably from approximately 12 to 18 French (4.0–6.0 mm diameter), and an overall length from approximately 60 to 120 cm, more preferably 70 to 90 cm, for femoral artery deployment in adult human patients. The catheter shaft 1502 is preferably formed of a flexible thermoplastic material, a thermoplastic elastomer, or a thermoset elastomer. Suitable materials for use in the elongated catheter include, but are not limited to, polyvinylchloride, polyurethane, polyethylene, polyamides, polyesters, silicone, latex, and alloys or copolymers thereof, as well as braided, coiled or counterwound wire or filament reinforced composites.

An upstream distal flow control member 1516, in this illustrative embodiment in the form of an inflatable porous root balloon, is mounted on the catheter shaft 1502 near the distal end 1506 by heat welding or with an adhesive. The porous root balloon 1516 has a deflated state in which the diameter of the porous root balloon is, preferably, not substantially larger than the diameter of the catheter shaft 1502. And, an inflated state in which the porous root balloon 1516 expands to a diameter sufficient to occlude blood flow in the aortic root of the patient. For use in adult humans, the porous root balloon 1516 preferably has an inflated outer diameter of approximately 2 to 5 cm. The catheter shaft 1502 is navigated transluminally into the ascending aorta until the porous root balloon 1516 is positioned in the aortic root. Thereafter, the delivery of cardioplegia to the coronary ostia is performed through a porous material 1532 while a non-porous material 1531 substantially occludes the ascending aorta. The material or materials used in the porous root balloon 1516 are preferably characterized by properties that allow an internal pressure within the porous root balloon 1516 to be maintained at a sufficient level to occlude the aorta, while also allowing a controlled volume of fluid to escape from the porous root balloon 1516 for perfusing the coronary arteries. Thus, the surface of the balloon may be porous, or have porous regions, or include apertures that allow cardioplegia to seep or flow at a known rate when a specific pressure is attained.

A downstream anchoring member 1518 is mounted proximal to the porous root balloon 1516 on the catheter shaft 1502. The distance between the porous root balloon 1516 and the downstream anchoring member 1518 is preferably between 3 and 20 cm, more preferably between 8 and 15 cm, and is chosen so that when the aortic catheter 1500 is deployed and the porous root balloon 1516 is positioned in the aortic root, the downstream anchoring member 1518 will be positioned in the descending aorta downstream of the left subclavian artery. The downstream anchoring member 1518 in this embodiment is in the form of an expandable, inflatable balloon bonded to the catheter shaft 1502 by heat welding or with an adhesive. The downstream anchoring member 1518 may be larger, the same size or smaller than the porous root balloon 1516. Of primary importance is the downstream anchoring member configuration that stabilizes the shaft 1502 and allows for the separation of the aorta for differential perfusion. Suitable materials for the inflatable balloon downstream anchoring member 1518 include flexible polymers and elastomers, which include, but are not limited to, polyvinylchloride, polyurethane, polyethylene, polypropylene, polyamides (nylons), polyesters, latex, silicone, and alloys, copolymers and reinforced composites thereof. In addition, the outer surface of the downstream anchoring member 1518 may include a friction increasing coating or texture to increase friction with the aortic wall when deployed.

The inflatable balloon downstream anchoring member 1518 has a deflated state, in which the diameter of the anchoring member 1518 is preferably not much larger than the diameter of the catheter shaft 1502, and an inflated state, in which the anchoring member 1518 expands to a diameter sufficient to regulate blood flow in the descending aorta of the patient. For use in adult human patients, the inflatable balloon downstream anchoring member 1518 preferably has an inflated outer diameter of approximately 1.5 cm to 5.0 cm and a length of approximately 3.5 cm to 7.5 cm. The more elongated form of the inflatable balloon downstream anchoring member 1518 creates greater anchoring friction against the wall of the descending aorta when the downstream anchoring member 1518 is inflated in order to prevent migration of the aortic catheter 1500 due to pressure gradients within the aorta during perfusion.

As shown in FIG. 16, which is a magnified lateral cross portion of the aortic catheter 1500 of FIG. 15 taken along line 16—16, the catheter shaft 1502 has five lumens: a corporeal perfusion lumen 1508, an arch perfusion lumen 1511, a pressure lumen 1512, a common cardioplegia/inflation lumen 1510, and a guide wire lumen 1514. The configuration of the lumens shown is for illustrative purposes only, and other configurations could be used. For example, in alternate embodiments the catheter shaft 1502 may not include a corporeal perfusion lumen 1508. In embodiments where a corporeal perfusion lumen is not provided corporeal flow can be accomplished by through an integral or nonintegral slidably disposed coaxial cannula or through a contralateral or collateral cannula. In addition, the catheter shaft may be configured to provide separate inflation lumens to provide individual inflation pressures in the balloons.

Referring now to FIGS. 15 and 16 the corporeal perfusion lumen 1508 extends through the catheter shaft 1502 from the proximal end 1504 to one or more perfusion ports 1536 on the exterior of the catheter shaft 1502 proximal to the porous root balloon 1516. The pressure lumen 1512 extends through the catheter shaft 1502 from the proximal end 1504 to a pressure port 1526 located proximal to the porous root balloon 1516 to monitor pressure near the aortic arch. The inflation/cardioplegia lumen 1510 extends through the catheter shaft 1502 from the proximal end 1504 to inflation/cardioplegia ports 1522 for inflation and deflation of the porous root balloon 1516 and the anchoring member 1518 with cardioplegia fluid. The guide wire lumen 1514 extends from the proximal end 1504 of the catheter shaft 1502 to a guide wire port 1536 at the distal end 1506 of the catheter shaft 1502, distal to the porous root balloon 1516. Attached to the proximal end 1504 of the catheter shaft 1502 is a manifold 1750 with fittings for each of the catheter lumens, which shall be described in more detail below with reference to FIG. 17.

The aortic catheter 1500 includes a distal radiopaque marker 1540 positioned near the distal end 1506 of the catheter shaft 1502, and an intermediate radiopaque marker 1542 positioned near the proximal edge of the porous root balloon 1516 and a proximal radiopaque marker 1544 located on the distal edge of the anchoring member 1518.

Figure 17:
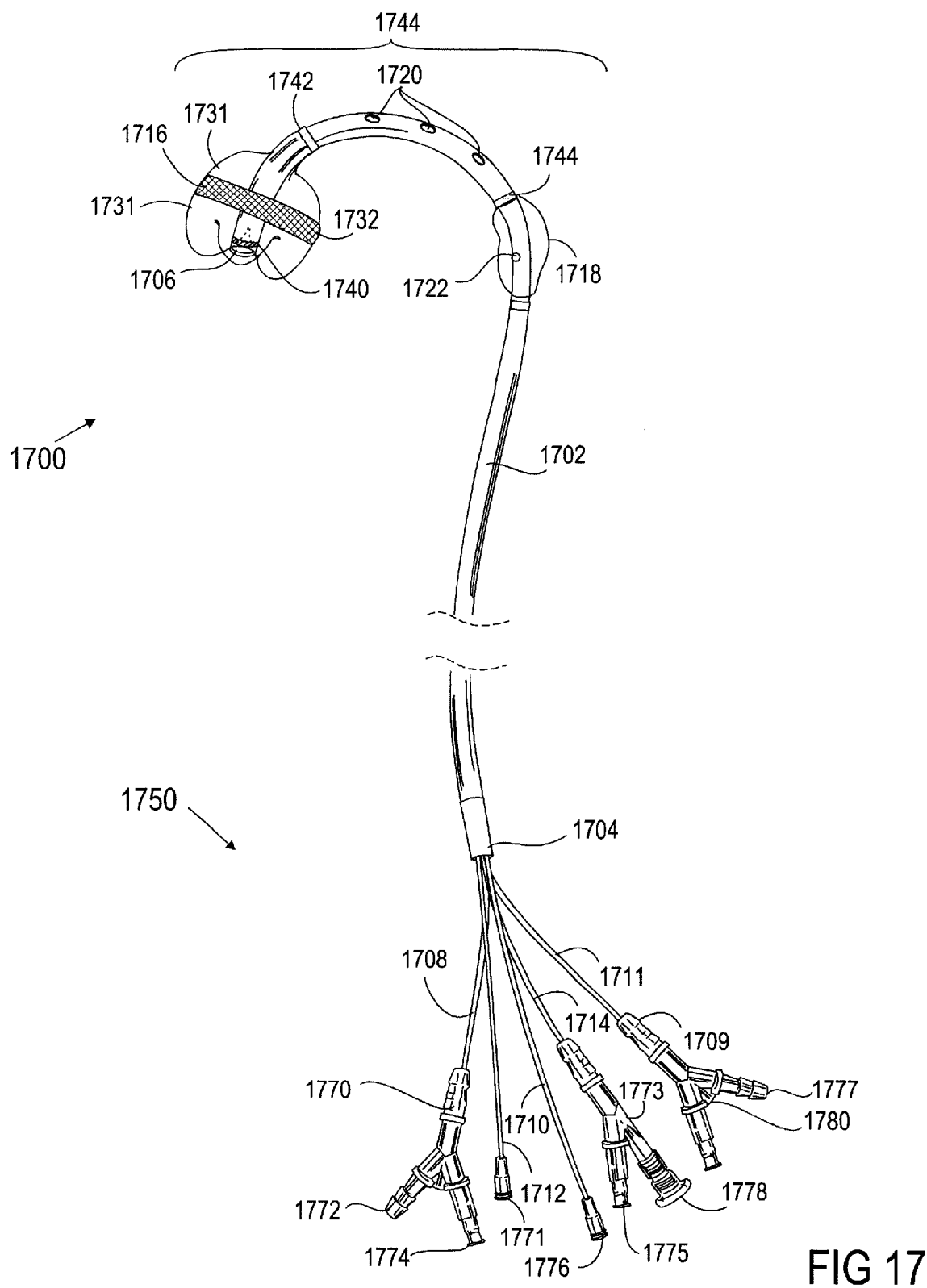
FIG. 17 shows a side view of an aortic catheter according to the present invention with a catheter shaft configured for retrograde deployment via femoral artery access.

FIG. 17 shows a side view of an aortic catheter 1700 according to the present invention with a catheter shaft 1702 configured for retrograde deployment via femoral artery access. In order to facilitate placement of the aortic catheter 1700 and to improve the stability of the catheter 1700 in the proper position in the patient's aorta, a distal region 1744 of the catheter shaft 1702 may be preshaped with a curve to match the internal curvature of the patient's aortic arch. The curved distal region 1744 represents a J-shaped curve of approximately 180 degrees of arc with a radius of curvature of approximately 2 to 4 cm to match the typical curvature of the aortic arch in an adult human patient. In addition, the distal end 1706 of the catheter may be skewed slightly up out of the plane of the curve to accommodate the forward angulation of the patient's ascending aorta. Additionally, the catheter shaft 1702 may be reinforced, particularly in the curved distal region 1744, for example with braided or coiled wire, to further improve the stability of the catheter 1700 in the proper position in the patient's aorta. The elongated catheter shaft 1702 is preferably formed of a flexible thermoplastic material, a thermoplastic elastomer, or a thermoset elastomer. Suitable materials for use in the elongated catheter include, but are not limited to, polyvinylchloride, polyurethane, polyethylene, polyamides, polyesters, silicone, latex, and alloys or copolymers thereof, as well as braided, coiled or counterwound wire or filament reinforced composites.

As mentioned above, the proximal end 1704 of the catheter shaft 1702 is connected to a manifold 1750 with fittings for each of the catheter lumens. The corporeal perfusion lumen 1708 is connected to a Y-fitting 1770 that has a barb connector 1772 for connection to a perfusion pump or the like and a luer connector 1774, which may be used for monitoring perfusion pressure, for withdrawing fluid samples or for injecting medications or other fluids. The pressure lumen 1712 is connected to a luer connector 1771 or other fitting suitable for connection to a pressure monitor. The inflation/cardioplegia lumen 1710 is connected to a luer connector 1776 or other fitting suitable for connection to a cardioplegia source. The guide wire lumen 1714 is connected to a Y-fitting 1773 that has a luer connector 1775 and a guide wire port 1778 with a Touhy-Borst adapter or other hemostasis valve. An arch perfusion lumen 1711 is connected to a Y-fitting 1709 having a barb connector 1777 for connection to a perfusion pump or the like and a luer connector 1780 which may be used for monitoring perfusion pressure, for withdrawing fluid samples or for injecting medications or other fluids. In addition, a separate coaxial arterial cannula may be implemented to perfuse the corporeal body in a retrograde direction eliminating the need for a corporeal perfusion lumen 1708 to minimize the catheter shaft outer diameter and simplifying the overall catheter design.

Figure 18:
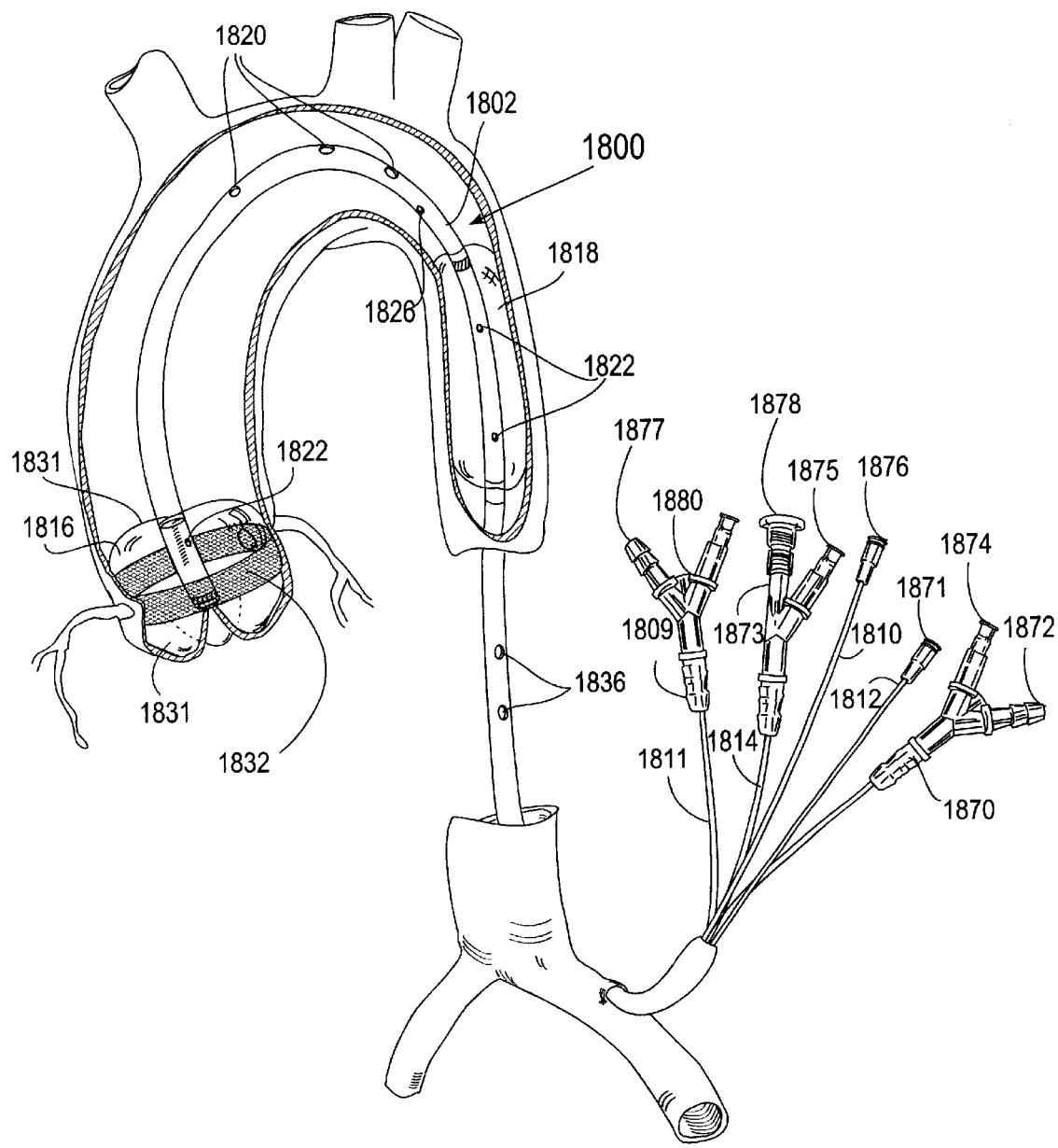
FIG. 18 is a schematic diagram showing an aortic catheter according to the present invention deployed within a patient's aorta via femoral artery access.

FIG. 18 is a schematic diagram showing an aortic catheter 1800 according to the present invention deployed within a patient's aorta via femoral artery access. The aortic catheter 1800 is introduced into the patient's circulatory system through a peripheral artery access, such as the femoral artery, by using the percutaneous Seldinger technique, through an introducer sheath or via an arterial cutdown. The catheter 1800 may optionally be introduced into the femoral artery through a coaxial arterial perfusion cannula (not shown). Meanwhile, one or more venous cannulae are introduced into the vena cavae via the femoral vein or the jugular vein. The aortic catheter 1800 is advanced up the descending aorta and across the aortic arch under fluoroscopic or ultrasound guidance with the aid of a guide wire within the guide wire lumen 1814. The aortic catheter 1800 is advanced until the distal flow control member 1816, in this illustrative embodiment in the form of a porous aortic root balloon, is positioned within the ascending aorta within the aortic root. The porous root balloon 1816 may be partially inflated enabling the porous root balloon to serve as an atraumatic bumper giving tactile feedback when the catheter has touched the aortic valve. In addition, the radiopaque markers can be referenced to establish proper placement of the porous root balloon 1816. Once proper placement is established, the guide wire is withdrawn.

Using a multihead cardiopulmonary bypass pump or the like, perfusion of oxygenated blood is started through the perfusion ports 1820 and 1836 (or separate arterial cannula). The porous root balloon 1816 and anchoring member 1818 are totally inflated with a cardioplegia solution to partition the aorta, whereupon a cardioplegic agent, such cold crystalloid cardioplegia or blood cardioplegia, is infused through the porous aortic root balloon 1816 to induce cardioplegic arrest. Generally, the porous root balloon 1816 will have an inflated diameter sufficient to occlude blood flow through the aortic root and the anchoring member will have sufficient diameter to engage the descending aortic wall to stabilize the catheter shaft 1802 in the aorta. Since the diameter of the aortic root is typically somewhat larger than the diameter of the ascending aorta, the fully inflated porous root balloon 1816 may thus be prevented from leaving the aorta by the sinotubular ridge and the aortic valve annulus.

Typically, during surgery, approximately 500 ml to 1,000 ml of cardioplegia is infused to the heart at an initial rate of 250 ml to 350 ml/minute to induce cardioplegic arrest. The flow is then typically continued intermittently, alternating between no flow of cardioplegia and a low flow of cardioplegia ranging from 25 to 250 ml/minute to prevent the heart from resuming a sinus rhythm until the operation is complete. Therefore, it is preferable that the flow rate of cardioplegia be controllable within a range from 0 ml to 500 ml/minute, and more preferably within a range from 0 ml to 350 ml/minute. Alternatively, an initial bolus of cardioplegia may be delivered by other known means such as a retrograde coronary sinus catheter, direct injection into the aortic root, injection into the coronary arteries, or other known means for infusing cardioplegia.

In one illustrative embodiment, the porous root balloon 1816 is shaped to conform somewhat to the shape of the aortic root, and may further conform to the shape of the aortic valve. As previously illustrated in FIG. 5 a three-lobed porous aortic root balloon 516 can be implemented. The lobes 599 are configured to support the cusps of the aortic valve and maintain the competence of the aortic valve against pressure in the aortic lumen. The three-lobed balloon embodiment can be easily incorporated into this or any embodiment disclosed herein. Alternatively, the porous root balloon 1816 may be compliant, or formed of a compliant material so that the inflated balloon conforms to the shape of the aortic valve when inflated.

The porous aortic root balloon 1816 is comprised of a non-porous portion 1831 where cardioplegic fluid is not allowed to seep therethrough and a porous portion 1832 where cardioplegic solution is allowed to seep therethrough. The size, shape, and position of the porous portion 1832 is for illustrative purposes only, any other desired sizes, shapes, or positions may be used. The porous portion 1832 and non-porous portion 1831 of the porous aortic root balloon 1816 may be formed from the same or separate materials. Suitable materials for the non-porous portions 1831 of the porous aortic root balloon 1816 include, but are not limited to, elastomers, thermoplastic elastomers, polyvinylchloride, polyurethane, polyethylene, polyamides, polyesters, silicone, latex, and alloys or copolymers and reinforced composites thereof. In addition, the outer surface of the porous aortic root balloon 1816 may include a force or friction increasing means such as a friction increasing coating or texture to increase friction between the porous aortic root balloon 1816 and the aortic wall when deployed. Suitable materials for the porous portion 1832 include, but are not limited to, a perforated polymer film, porous or microporous membranes, TYVEK (spun-bonded polyethylene), expanded PTFE (GORTEX), woven or knit mesh or fabric, or the like.

A selected fluid, such as a cardioplegia fluid, is introduced into the porous aortic root balloon 1816 by way of the inflation/cardioplegia lumen 1810. Any acceptable cardioplegia fluid may be used, such as cold crystalloid cardioplegia, normothermic blood cardioplegia, or hypothermic blood cardioplegia. In an alternate embodiment, it may be preferable to prime the balloon with a more viscous solution, for example a radiopaque contrast agent mixed with saline solution or with cardioplegic solution, that is, to initially inflate the balloon with a solution that will leak from the balloon at a rate slower than the cardioplegia solution will leak. When the porous root balloon 1816 is fully inflated, the porous portion 1832 should be positioned over the coronary ostia. It is possible, but uncommon, for a heart to have more than two coronary ostia. The number and positioning of the porous portion 1832 may be selected to compensate for this or other unusual anatomical arrangements. When the correct pressure is attained, the porous aortic root balloon 1816 occludes blood flow through the aortic lumen. The cardioplegia fluid used to inflate the porous aortic root balloon 1816 seeps through the porous portion 1832 at a known rate into the coronary arteries. The flow rate may be adjustable by adjusting the pressure within the porous aortic root balloon 1816. The competence of the aortic valve is not challenged because the cardioplegic fluid is delivered directly to the coronary arteries, thus preferably the aortic valve does not experience significant retrograde fluid pressure. The porous aortic root balloon 1816 prevents seepage of cardioplegia fluid through the porous portion 1832 by contact between the aortic wall and the portions of porous windows 1832 not aligned with the coronary ostia. Preferably, only the areas in contact with the coronary ostia are capable of delivering cardioplegia since this is the only area with an open space for the fluid to travel.

Perfusion of the patient is maintained through the perfusion ports 1820 and 1836 (and/or arterial cannula) and cardioplegic arrest is maintained by continued infusion of the cardioplegic agent through the porous aortic root balloon 1816 for as long as necessary for completion of the surgical procedure using minimally invasive or standard open-chest techniques. Perfusion temperatures, perfusate compositions and flow rates may be optimized to each of the segmented regions of the patient's circulation for optimal organ preservation while on cardiopulmonary bypass. While the aortic catheter 1800 is deployed, the anchoring member 1818 stabilizes and anchors the catheter shaft 1802 and prevents upstream or downstream migration of the catheter 1800 or the porous root balloon 1816 due to differential pressures within the aorta. At the completion of the surgical procedure, the porous aortic root balloon 1816 is deflated to allow oxygenated blood to flow into the patient's coronary arteries, whereupon the heart should spontaneously resume normal sinus rhythm. If necessary, cardioversion or defibrillation shocks may be applied to restart the heart. The patient is then weaned off of bypass and the aortic catheter 1800 and any other cannulae are withdrawn.

Figure 19:
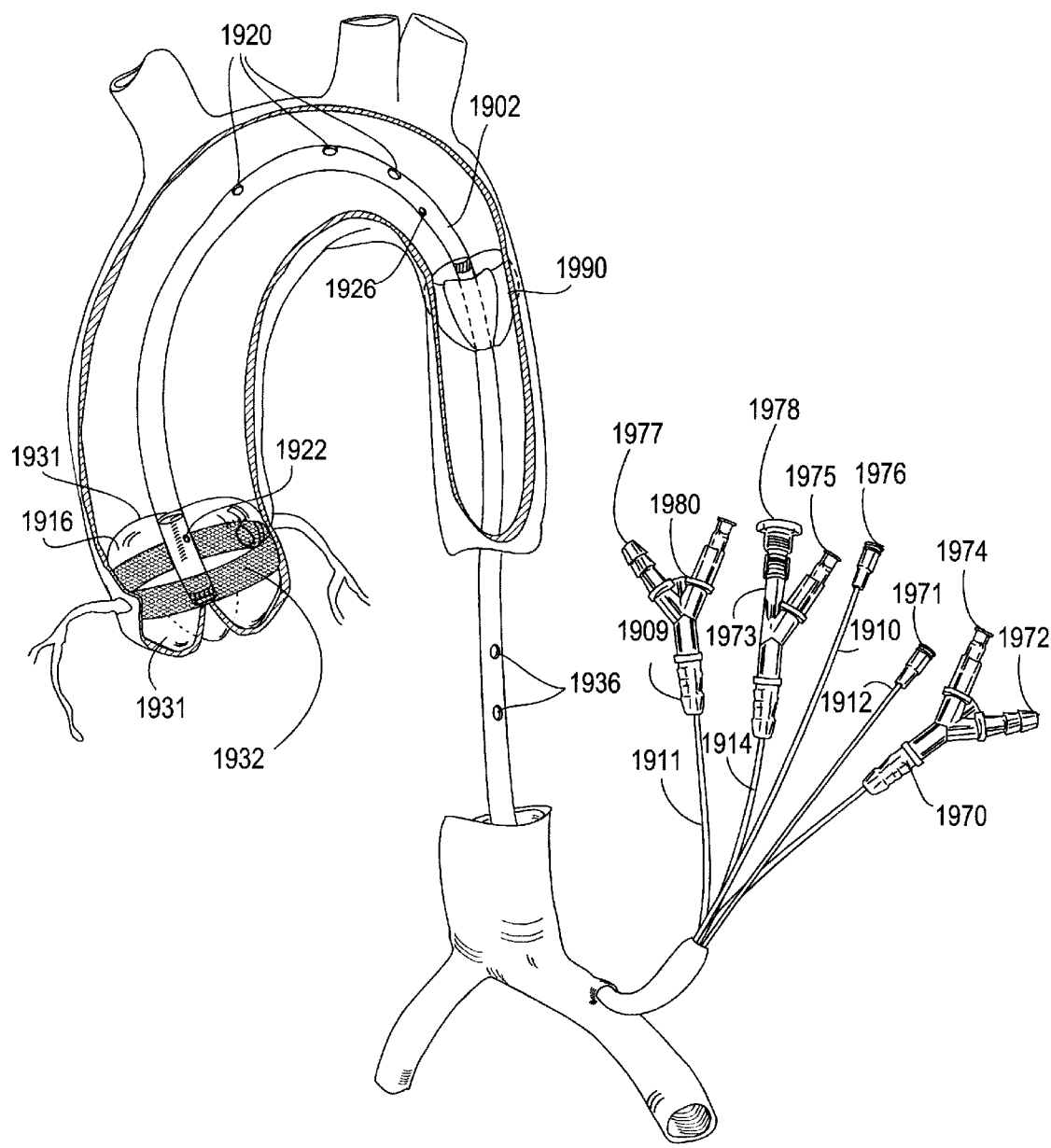
FIG. 19 is a schematic diagram showing a tenth embodiment of the aortic catheter system of the present invention deployed within a patient's aorta having a flow control valve positioned in the descending aorta rather than an anchoring balloon.

FIG. 19 is a schematic diagram showing a tenth embodiment of the aortic catheter system of the present invention deployed within a patient's aorta, in a configuration similar to that explained above relating to FIG. 18, but having a flow control valve 1990 positioned in the descending aorta rather than an anchoring balloon. The valve 1990 performs the function of partitioning the aorta providing the possibility of differential perfusion of the partitioned circulatory system. Any desirable or practical collapsible/deployable valve may be used. Examples of useable collapsible/deployable valves have been previously described in U.S. Pat. Nos. 5,827,237 and 5,833,671 and U.S. patent application Ser. No. 08/665,635, by John A. Macoviak and Michael Ross all previously incorporated herein by reference.

The embodiments of the porous aortic root balloon described above have focused on the perfusion of cardioplegia to the coronary arteries. However, other selected fluids may be perfused to the coronary arteries including streptokinase, tPA, or urokinase for thrombolysis, blood and blood substitutes such as PERFLUBRON or other perfluorocarbon compounds, and radiopaque dyes for angiography.

What is claimed is:

1. An aortic catheter comprising:
an elongated catheter shaft configured for introduction into a patient's aorta and having a proximal end and a distal end, a flow control member coupled to said elongated catheter having an expanded diameter sufficient to block blood flow through the patient's aortic root when inflated, said flow control member having a distal surface with three lobes extending distally therefrom, said flow control member comprising at least one permeable portion; whereby a fluid used to inflate said flow control member may seep through said at least one permeable portion.

2. The aortic catheter of claim 1, further comprising a downstream anchoring member spaced apart from said flow control member.

3. The aortic catheter of claim 2, further comprising a perfusion lumen extending through said elongated catheter shaft from said proximal end to at least one perfusion port on said elongated catheter shaft between said flow control member and said downstream anchoring member.

4. The aortic catheter of claim 3, further comprising a second perfusion lumen extending through said elongated catheter shaft from said proximal end to at least one perfusion port on said elongated catheter shaft proximal to said downstream anchoring member.

5. The aortic catheter of claim 2, wherein said downstream anchoring member is in the form of a balloon.

6. The aortic catheter of claim 2, wherein said downstream anchoring member is in the form of a valve.

7. The aortic catheter of claim 1, wherein said flow control member is configured such that the flow control member when inflated in the aortic root is restricted from moving out of the aortic root by the patient's sinotubular ridge and a aortic valve annulus.

8. The aortic catheter of claim 1, wherein said flow control member is configured to conform to the shape of the aortic root.

9. The aortic catheter of claim 8, wherein said flow control member is further configured to conform to a shape of the cusps of the aortic valve.

10. The aortic catheter of claim 1, wherein said at least one permeable portion comprises a plurality of porous windows.

11. The aortic catheter of claim 1, wherein said at least one permeable portion comprises a circumferential porous strip.

12. The aortic catheter of claim 1, wherein said at least one permeable portion comprises pressure valves.

13. The aortic catheter of claim 1, wherein said at least one permeable portion comprises a multiplicity of bistable nipples.

14. The aortic catheter of claim 1, wherein said at least one permeable portion comprises a multiplicity of bistable nipples.

15. The aortic catheter of claim 1, wherein said flow control member comprises three lobed portions longitudinally aligned with respect to said elongated catheter shaft.

16. The aortic catheter of claim 1, wherein said flow control member comprises two inflatable balloons.

17. The aortic catheter of claim 1, further comprising a perfusion lumen extending through said elongated catheter shaft from said proximal end to at least one perfusion port on said elongated catheter shaft proximal to said flow control member.

18. The aortic catheter of claim 1, wherein said at least one permeable portion provides fluid flow at a variable rate.

19. The aortic catheter of claim 18, wherein the flow rate is correlated to a fluid pressure inside said flow control member.

20. The aortic catheter of claim 1, further comprising a distal impermeable portion, a middle permeable portion and a proximal impermeable portion.

21. The aortic catheter of claim 1, wherein the permeable portion is surrounded by an impermeable portion.

22. The aortic catheter of claim 1, wherein the permeable portion is comprised of at least one bistable nipple.

23. The aortic catheter of claim 1, further comprising a second lumen in fluid communication with a proximal opening and a distal port, the second lumen configured to be coupled to a CPB machine to perfuse oxygenated blood to a patient's arterial system.

24. The aortic catheter of claim 1, wherein the flow control member is comprised of at least one balloon.

\* \* \* \* \*